United States Patent [19]

Maddock et al.

[11] Patent Number: 5,549,672
[45] Date of Patent: Aug. 27, 1996

[54] METHOD AND APPARATUS FOR FILLING MAMMARY PROSTHESES AND TISSUE EXPANDERS

[75] Inventors: Julie Maddock, Santa Barbara; Robert Bley, Goleta; Patricia Altavilla, Santa Barbara, all of Calif.

[73] Assignee: Mentor Corporation, Santa Barbara, Calif.

[21] Appl. No.: 238,981

[22] Filed: May 6, 1994

Related U.S. Application Data

[63] Continuation of Ser. No. 814,376, Dec. 26, 1991.

[51] Int. Cl.⁶ .................................................... A61F 2/12
[52] U.S. Cl. ................... 623/8; 623/11; 604/141
[58] Field of Search ........................ 623/7, 8; 604/141, 604/142

[56] References Cited

U.S. PATENT DOCUMENTS

| | | | |
|---|---|---|---|
| 3,153,414 | 10/1964 | Beall et al. | 604/142 |
| 3,838,794 | 10/1974 | Cogley et al. | 604/141 |
| 3,883,902 | 5/1975 | Lynch | 623/8 |
| 3,919,724 | 11/1975 | Sanders et al. | 623/8 |
| 4,090,514 | 5/1978 | Hinck et al. | 604/142 |
| 4,143,428 | 3/1979 | Cohen | 623/8 |
| 4,507,116 | 3/1985 | Leibinsohn | 604/142 |
| 4,624,671 | 11/1986 | Kress | 623/8 |
| 4,735,613 | 4/1988 | Bellin et al. | 604/142 |
| 4,955,905 | 9/1990 | Reed | 623/8 |
| 4,955,906 | 9/1990 | Coggins et al. | 623/8 |
| 5,059,182 | 10/1991 | Laing | 604/142 |
| 5,219,360 | 6/1993 | Georgiade | 623/8 |

FOREIGN PATENT DOCUMENTS

| | | | |
|---|---|---|---|
| 2042091 | 9/1980 | United Kingdom | 604/141 |

*Primary Examiner*—David Isabella
*Assistant Examiner*—Laura Fossum
*Attorney, Agent, or Firm*—Blakely, Sokoloff, Taylor & Zafman

[57] ABSTRACT

Method and apparatus for filling mammary prostheses and tissue expanders using pumping systems are disclosed. In accordance with the method, a pumping system is used to deliver flow at the desired flow rate or pressure through a tube to the injection needle, allowing the surgeon to concentrate his attention on the injection itself to fill the inflatable mammary prosthesis or the tissue expander without having to operate and count filling syringes, all in a much faster manner than in the prior art. The pumping system used may include fluid volume measuring capabilities, pressure measuring capabilities, and other capabilities such as the capability, for viscosity reduction purposes, of heating the fluid to a temperature still compatible with injection. By providing the fluid in an appropriate bag with flexible tubing attached thereto, all in a sterile condition, the injection system and method of the invention provides a substantially closed system allowing fast and accurate filling of a mammary prosthesis or tissue expander with minimal opportunity for infection. Alternate methods and apparatus are disclosed.

15 Claims, 3 Drawing Sheets

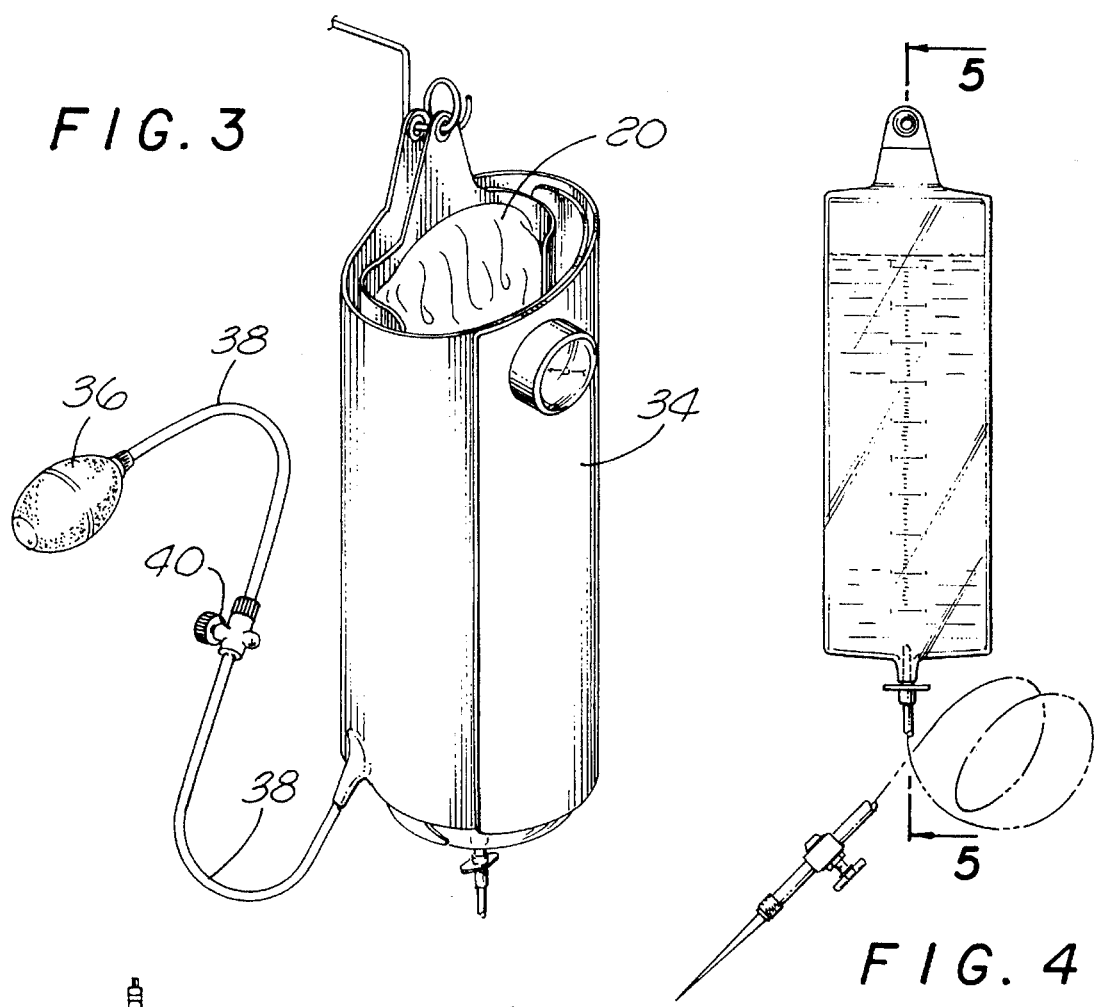
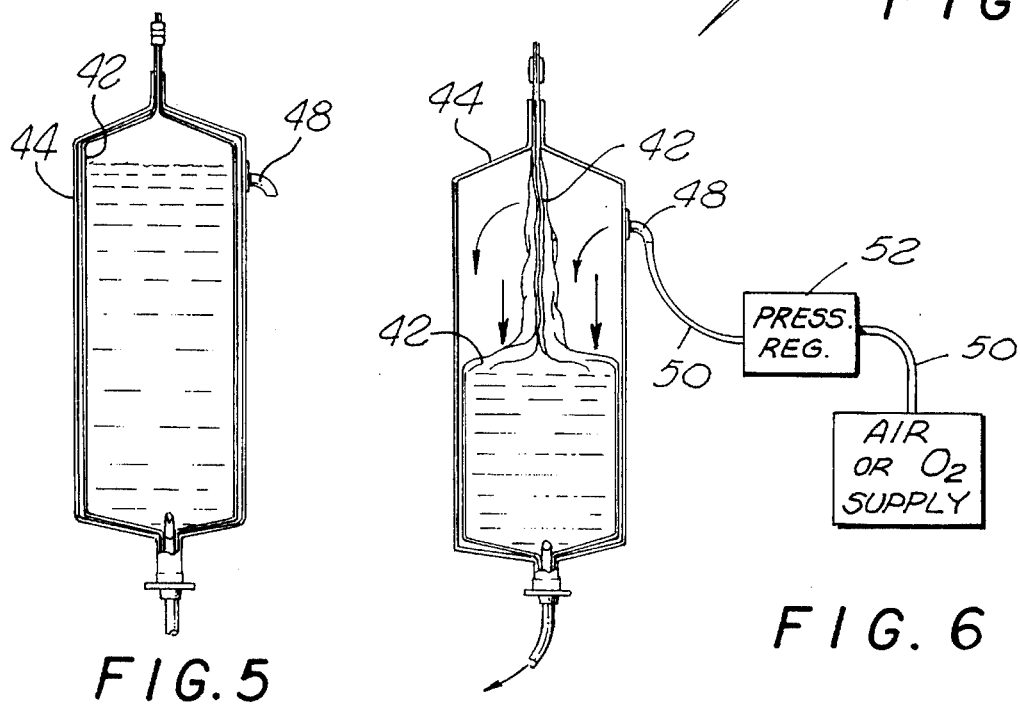
FIG. 3
FIG. 4
FIG. 5
FIG. 6

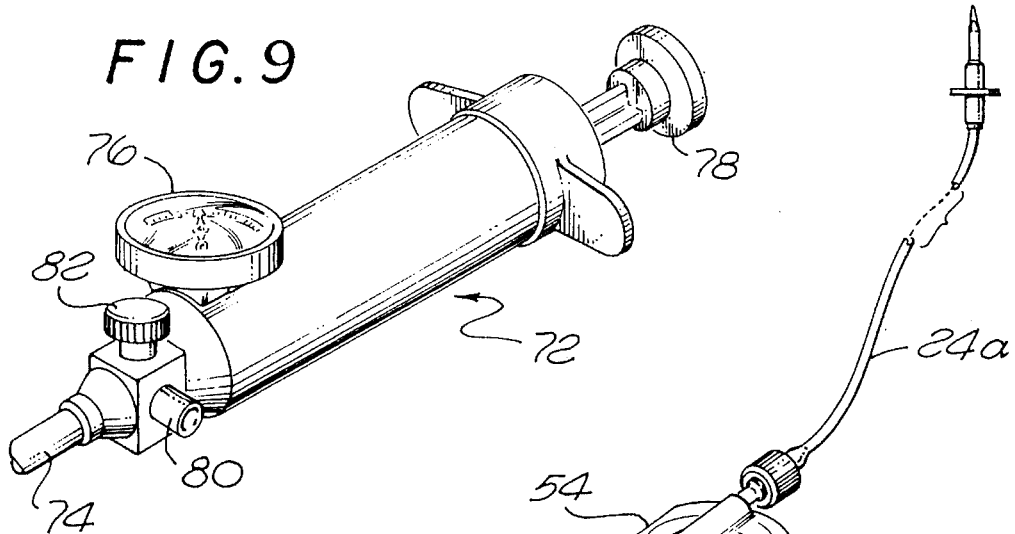
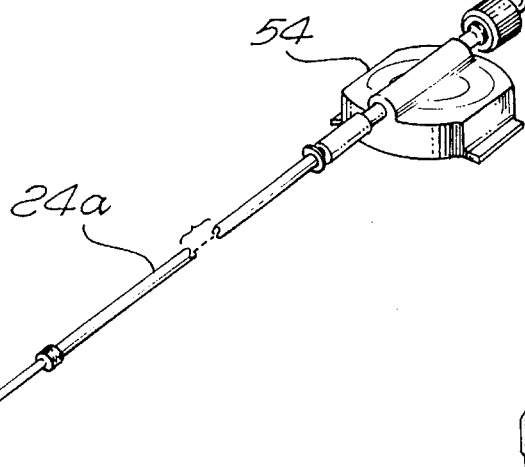
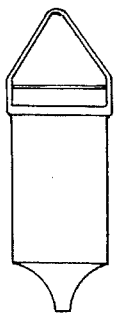
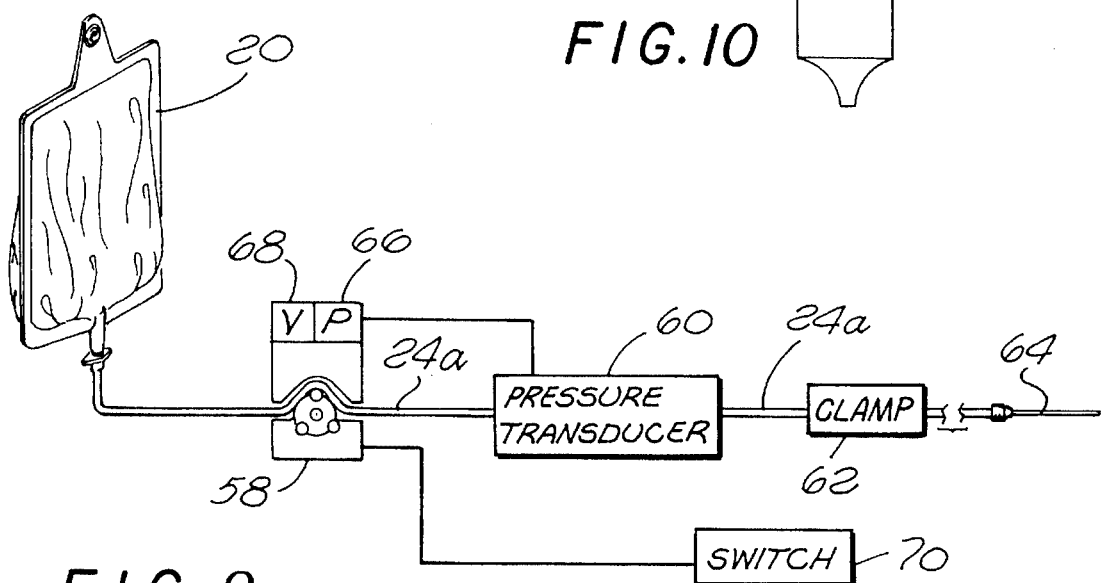

METHOD AND APPARATUS FOR FILLING MAMMARY PROSTHESES AND TISSUE EXPANDERS

This is a continuation of pending prior application Ser. No. 07/814,376 filed on Dec. 26, 1991 for METHOD AND APPARATUS FOR FILLING MAMMARY PROSTHESES AND TISSUE EXPANDERS.

BACKGROUND OF THE INVENTION

1. Field Of The Invention

The present invention relates to the field of inflatable prostheses and tissue expanders.

2. Description Of Related Art

Inflatable mammary prostheses and tissue expanders are well known in the prior art. In the case of an inflatable mammary prosthesis, the prosthesis is normally inserted through a small incision substantially under the patient's arm. To allow the prosthesis to pass through the small incision, the air filled prosthesis is normally substantially deflated by aspirating the same with an empty, sterile syringe. At this point, some surgeons prefer to add some of the intended inflation fluid to the prosthesis, primarily to displace the remaining air with fluid as opposed to inflating the prosthesis to any substantial extent. In any event, then the prosthesis is folded and inserted into a surgically prepared pocket. Once implanted of course, the prosthesis must be inflated to provide the desired resulting aesthetic appearance.

The conventional method of inflating a breast prosthesis, once implanted, is to use a conventional syringe to inject the filling fluid through an appropriate fill port on the prosthesis. Since a mammary prosthesis is commonly relatively large compared to conventional syringes, a number of syringe injections are required, usually achieved by the repeated refilling of one syringe as opposed to the use of a plurality of prefilled syringes. Thus, to accurately control the amount of fluid being used to inflate the prosthesis, the syringe must not only be accurately and repetitively refilled, but the surgeon must count the number of syringe injections for each prosthesis. While the count is not large in itself, the environment and other things needing or diverting the surgeon's attention can easily result in an error in the count of syringe injections used to fill any particular breast prosthesis. Further, manually injecting all of the fluid from a filled syringe a number of times for each breast prosthesis can be fatiguing for the surgeon, and time consuming as thumb pressure on the syringe wanes over a period of time. Of course the longer the inflation takes, the longer the incision is open and the greater the risk of infection. Further, of course, the refilling of the syringe itself can be fatiguing and offers the possibility of intrusion and contamination by bacteria and other foreign matter. Finally, it is not uncommon for the surgeon or assistant to fill the syringe from an open bowl of the filling fluid, perhaps making the filling of the syringes a little easier, but enhancing the possibility of intrusion of bacteria and other contamination into the inflation fluid.

In the case of tissue expanders, the same are normally surgically inserted into the region desired in a substantially uninflated state, and the incision allowed to heal. Thereafter, the tissue expander is itself expanded by injecting fluid through a filling port on the tissue expander using a conventional hypodermic needle passing through the skin of the patient. The tissue expander frequently is not inflated to the desired final state of inflation in a single injection, but rather is inflated through smaller periodic injections extending over a significant period of time so that the tissue is gradually stretched or expanded to achieve the desired result. Obviously, a very large number of very small expansion increments would be ideal, but this would take an excessive amount of time of the doctor and patient alike, and unnecessarily extend the total inflation time. On the other hand, typically there is a limit to the amount the tissue expander can be inflated at any one time without causing pain to the patient, and perhaps injury to the tissue itself, so that typically some number of inflation increments are required to ultimately achieve the desired result. Since the pain or discomfort experienced by the patient generally relates to the pressure in the tissue expander, each filling increment could be limited to a pressure approaching, though below the recognized threshold of pain or discomfort by the patient if the pressure within the tissue expander could be measured. However, since conventional syringes have no pressure measuring capability, and to achieve substantial flow rates the pressure within the syringe body itself is purposely made substantially higher than the threshold of pain by the thumb pressure of the doctor, current practice is to add fluid to the tissue expander until the patient is conscious of the onslaught of discomfort or pain, ultimately limited, of course, to the desired expansion of the tissue expander for aesthetic or other purposes. Syringes having a pressure measuring capability are known, but such devices are of a high, not low pressure capability, being used to inflate collapsible but substantially inelastic balloons such as prostate dilation balloons.

In the case of both tissue expanders and inflatable breast prostheses, it would be desirable to be able to inflate the same rapidly, accurately, with minimum chance of infection or foreign matter intrusion, and without inflation to a pressure that induces pain or discomfort to the patient.

SUMMARY OF THE INVENTION

Methods and apparatus for filling mammary prostheses and tissue expanders using pumping systems are disclosed. In accordance with the method, a pumping system is used to deliver flow at the desired flow rate or pressure through a tube to the injection needle, allowing the surgeon to concentrate his attention on the injection itself to fill the inflatable mammary prosthesis or the tissue expander without having to operate and count the refilling of syringes, all in a much faster manner than in the prior art. The pumping system used may include fluid volume measuring capabilities, pressure measuring capabilities, and other capabilities such as the capability, for viscosity reduction purposes, of heating the fluid to a temperature still compatible with injection. By providing the fluid in an appropriate bag with flexible tubing attachable or attached thereto, all in a sterile condition, the injection system and method of the invention provides a substantially closed system allowing fast and accurate filling of a mammary prosthesis or tissue expander with minimal opportunity for infection. Alternate methods and apparatus are disclosed.

BRIEF DESCRIPTION OF THE DRAWINGS

FIG. 3 illustrates the flexible container of FIG. 1 together with an inflatable cuff on an IV stand ready for delivery of the inflation fluid therein.

FIG. 4 illustrates a double wall inflatable flexible container and fill tube together with a volume scale thereon, the container containing a fluid suitable for inflating breast prostheses and tissue expanders and being in the form of a large tube within a tube heat sealed at the top and bottom thereof.

FIG. 5 is a cross section of the double wall inflatable flexible container and fill tube of FIG. 4.

FIG. 6 is a cross section of the double wall inflatable flexible container and fill tube of FIG. 4 as partially emptied during inflation of an inflatable prosthesis.

FIG. 7 illustrates a fill tube having a pressure transducer sensor preassembled in the fill tube line.

FIG. 8 illustrates a system utilizing the fill tube of FIG. 7 and flexible container of FIG. 1 together with a peristaltic pump, pressure readout, volume readout and pump control.

FIG. 9 illustrates a syringe with a low range pressure gage thereon suitable for use in inflating mammary prostheses and tissue expanders, and which in turn may be refilled in any of a number of ways.

FIG. 10 illustrates a container containing a propellant for inflation fluid either in the container or in a separate container.

DETAILED DESCRIPTION OF THE INVENTION

Figure 1:
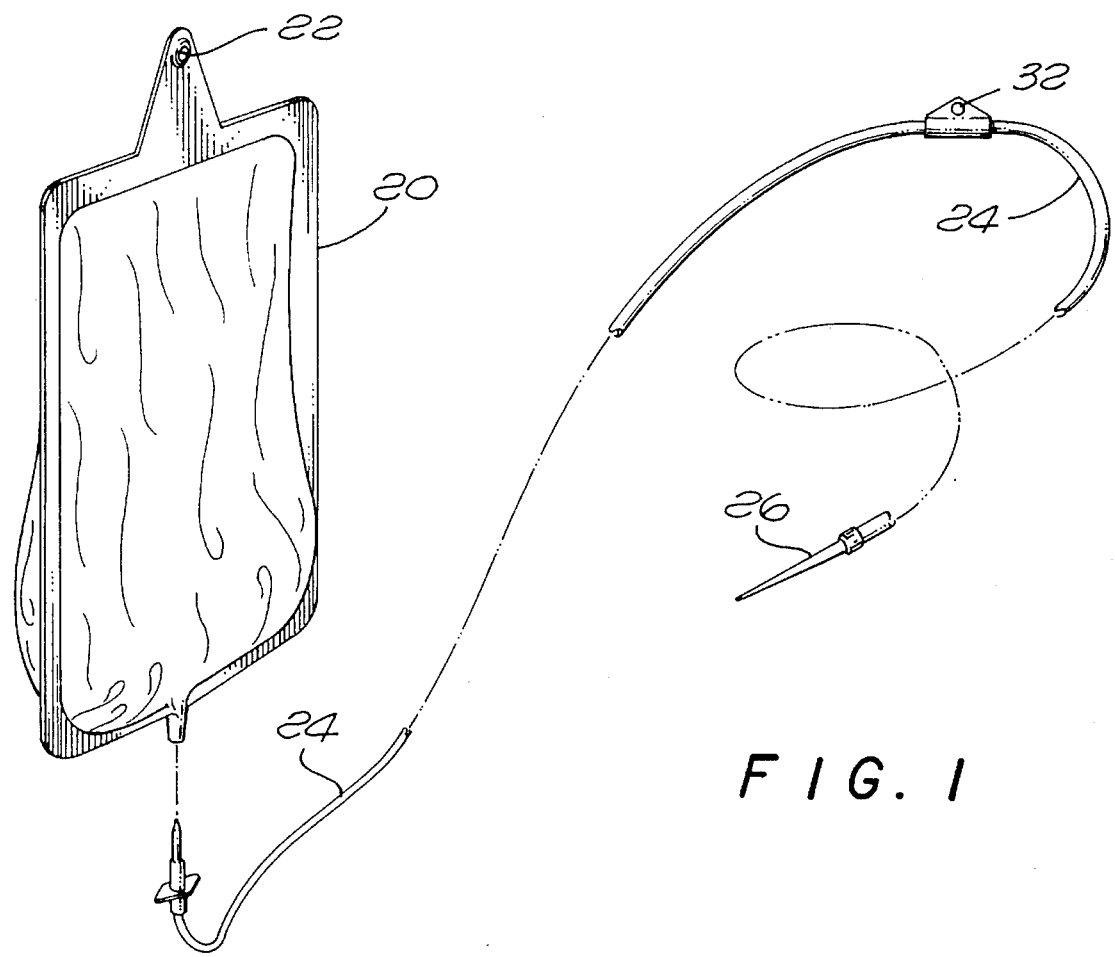
FIG. 1 illustrates a flexible container and fill tube, the flexible container containing a fluid suitable for inflating breast prostheses and tissue expanders.

First referring to FIG. 1, there is shown therein a fluid container 20 in the form of a flexible, preferably clear plastic bag containing a fluid for filling an inflatable breast prosthesis or tissue expander, such as by way of example, an isotonic saline solution or a solution with a higher viscosity such as polyvinylpyrrolidone, polyvinylalcohol, polysacharrides, peanut oil or the like. At one end of the container is an IV stand mount 22 allowing the container to be conveniently hung on an IV stand for use. At the other end of container 20 is a port 28 for connecting to a flexible tube 24 to provide communication with the interior of the container 20, the tube 24 being of a length of approximately 3 to 6 feet and having a smaller tube 26 at the distal end thereof suitable for engaging a cooperative fill port on a breast prosthesis or tissue expander. The tube 24 may be connected to the port 28 on container 20 at the time of manufacture, though preferably the tube is supplied as a separate part in the inflation kit and includes a piercing spike on one end to pierce a seal in the container port 28 at the time the inflation kit is used by the surgeon. Such ports and piercing spikes are well known in the medical field for IV bags and the like and therefore are not described in further detail herein.

The tube 26 may be of any suitable material, typically rigid or at least semi-rigid, with a stainless steel tube being preferred for its strength and other properties which allow a large inner diameter for a given outer diameter, the outer diameter being limited by the inflatable device fill port size. This provides a lower pressure drop as the fluid flows through tube 26, or alternatively, a higher flow rate for a given pressure drop. If desired, a clip 32 may be provided for supporting flexible tube 24 at some intermediate point if and when desired.

Figure 2:
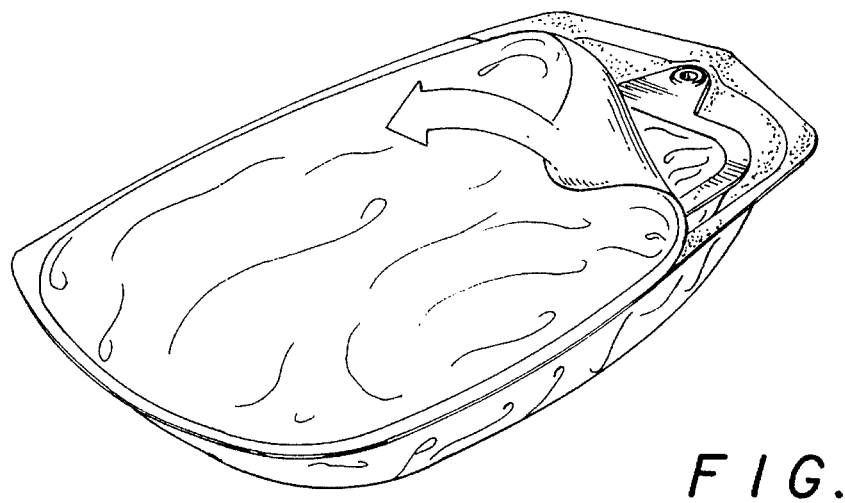
FIG. 2 illustrates the product of FIG. 1 as packaged in a sterile condition within a sealed outer enclosure.

The filled container as well as the tube assembly of FIG. 1 is provided in a sterile condition and sealed within an outer package, as shown in FIG. 2. Thus the outer package may be opened and the contents used to fill a breast prosthesis or tissue expander without the need for an open container of filling fluid, pouring the same into an open bowl, filling syringes, etc. In that regard, in the case of tissue expanders, a patient will typically feel a certain amount of pain or discomfort when a pressure of approximately 60 to 80 mm Hg has been reached. This pressure corresponds to an elevation of the fluid container above the tissue expander in the range of approximately 2½ to 3½ feet. Accordingly, with the tube 24 being sufficiently long for easy manipulation, such as 5 or 6 feet, and with the fluid container appropriately elevated, the desired pressure for a tissue expander may be automatically achieved. However, the rate of flow that would be achieved through the long tube 24 and the small delivery tube 26 would be quite limited because of the low differential delivery pressure, and of course, would continually slow as the pressure in the tissue expander increased, making a pure gravity feed undesirable and unnecessarily time consuming in at least many applications.

Accordingly, in accordance with one aspect of the present invention, an inflatable cuff is provided which may also be hung on an IV stand and which may be made to encircle the fluid container 20 as shown in FIG. 3. As shown therein, the fluid container 20 and the cuff 34 each have an IV stand hanger so that the two are individually supportable, though if desired, the fluid container may be mounted relative to the cuff by an appropriate hook or otherwise, with the cuff itself in turn being supported on the IV pole. In either case, inflation of the cuff to apply pressure on the fluid container and thus pressurize the fluid therein is provided through an inflation bulb 36 attached to the cuff through a line 38, with an in-line valve 40 (rotary, push button or otherwise) being provided to allow the venting of the cuff to facilitate the placement of a fluid container therein and/or the removal of a fluid container therefrom after use of the system.

As an alternative to the foregoing, the fluid container 20 may be in the form of a double walled heat sealed package as shown in FIGS. 4, 5 and 6. Here, formed as one unitary assembly, is a double walled flexible container in the form of a tube within a tube, heat sealed at the top and bottom to define an inner enclosure 42 containing the filling fluid and a sealed outer enclosure 44 therearound. The enclosure 42 is of course in fluid communication with delivery port 30, with the outer enclosure 44 being in communication with a pressurizing port 48 for connecting to a source of pressure, such as by way of example, an inflation bulb and associated line and venting valve such as bulb 36, line 38 and venting valve 40 of FIG. 3. As an alternative, usually low pressure air or oxygen or both are available wherever minor surgery is being performed, so that at least in the case of inserting and filling breast implants, low pressure air and/or oxygen will generally be available. Accordingly, as an alternative to the use of an inflation bulb, one might connect the outer container 44 to a source of air or oxygen through a line 50 as shown in FIG. 6, typically through a preset or variable pressure regulator 52, to provide the appropriate pressure to the outer container to pressurize the fluid in the inner container. Of course, as a further alternative, the cuff shown in FIG. 3 might itself be pressurized by an available local source of low pressure air or oxygen, as opposed to being pressurized by an inflation bulb. The use of the local source of air or oxygen has the advantage of substantially uniformly pressurizing the inflation fluid from the beginning to the end of its delivery, in comparison to the use of an inflation bulb wherein repeated reinflation of the fluid pressurizing device will be required if even a course approximation of a uniform pressure in the inflation fluid being delivered is desired.

In any case, as the inflation fluid is delivered from the inner enclosure, the remaining fluid will puddle at the bottom of the inner enclosure, so that if initially packaged with some air space above the fluid, the emptied portion of the inner container will collapse and the fluid level will be observable through the clear plastic walls of the containers. (The inner enclosure acts as a bladder, not as a pressure container, and therefore can be much thinner than the outer enclosure, more readily facilitating the puddling of the fluid at the bottom thereof and the collapse of the upper portion thereof as it is emptied.) Thus, using the scale printed on the wall of one of the containers as shown in FIG. 5, the surgeon can at all times determine the amount of fluid delivered and the fluid remaining, even when the space between the inner and outer containers is pressurized for fluid delivery.

Now referring to FIG. 7, an alternate embodiment of the fill tube for present invention may be seen. As shown in this figure, flexible tube 24a has a pressure transducer sensor unit 54 preconnected in series therewith so as to be part of the sterilized, prefilled kit provided by the manufacturer in a sterilized package, such as that shown in FIG. 2, so that upon opening of the sterilized package, the sensor unit 54 may be connected to the electrical unit of the pressure transducer to provide an electrical measurement of fluid pressure in the line. Pressure transducers (or gauges) of the foregoing type are readily commercially available, being comprised of two components, one which may be sterilized and in contact with the sterile fluid within which the pressure is to be measured, and a second which is not in contact with the sterile fluid, but rather senses the pressure of the sterile fluid through a flexible wall of the first member and provides an electrical output responsive to the same.

A system for using the embodiment of FIG. 7 may be seen in FIG. 8. In this embodiment, a peristaltic pump 58 is provided which delivers the inflation fluid to the pressure transducer assembly 60 and a manually operable clamp 62 and then to the actual inflation tube 64 penetrating the fill port on the prosthesis for the actual filling of the same. The clamp may be placed over the flexible line 24a, or alternatively provided as part of the assembly of FIG. 7. The pump may include an optional heater for heating the inflation fluid to approximately body temperature. While this is not essential to inflation of a tissue expander or a breast prosthesis, it is desirable to knowingly have the inflation fluid within a temperature range suitable for inflation of a prosthesis, and further for reducing the viscosity of the inflation fluid to increase the flow rate thereof for a given driving force or pressure. Obviously of course, a heater may be used in conjunction with other embodiments of the present invention such as that of FIGS. 3 and 6.

Clamp 62, as stated before, may be a simple clamp for squeezing and clamping off flexible tube 24a, or some form of valve in the line for turning the flow on and off. In that regard, such a valve might be provided as a three-way valve having an off position, a position providing inflation fluid communication through line 24a to the inflation tube 64, and a third position coupling line 24a to a separate outlet port from which syringes could be filled if desired by the surgeon.

The peristaltic pump 58, schematically represented in FIG. 8, is a positive displacement pump, pumping fluid through flexible tube 24a as a result of a plurality of rollers on a rotating head in effect rolling along the flexible tube at spaced apart locations. Thus, the volume of the inflation fluid pumped by the pump is directly proportional to the total rotation of the pump head. Consequently a programmable pump may be used wherein the pump will automatically shut off after a given volume of fluid has been pumped, thereby providing a direct and accurate measure of the inflation fluid delivered through inflation tube 64 to the prosthesis. Similarly, the pressure transducer assembly 60 may provide an electrical signal to display the pressure in the line as a visual readout, such as display 66 displaying the line pressure beside a display 68 for displaying the volume delivered (proportional to total pump head rotation). Similarly, the output of the pressure transducer assembly 60 may also or alternatively be used to automatically stop pump 58 when the pressure exceeds a predetermined limit so that the surgeon may, in effect, control the pump by control of flow through clamp or valve 62. Finally in addition, in the embodiment shown, a switch 70 (hand or foot operated) is provided so that the surgeon can control the pump separate and apart from control of the clamp or valve 62. In that regard, normally pressure transducer 60 will not provide an accurate measure of the pressure within the prosthesis during inflation, as the pressure in line 24a needs to be raised substantially above the pressure in the prosthesis to obtain adequate flow of inflation fluid through inflation tube 64. By control of pump 58 through switch 70, the pressure can be accurately measured however, as the pressures in pump 58, inflation tube 64 and the prosthesis will quickly equalize when pump 58 is momentarily turned off. Accordingly, the system of FIG. 8 is capable of heating the inflation fluid prior to delivery, of being programmed to deliver a selected volume of inflation fluid, to provide an accurate measurement of fluid pressure within the inflatable prosthesis at various times during the inflation process, of providing an independent manual control of the pump through switch 70, and of providing a simple in-line control of the pump through clamp or valve 62.

The embodiment of FIG. 8, or other similar embodiments, are advantageous in that the peristaltic pump provides an accurate measure of the volume delivered so that accurate partial delivery of the fluid within container 20 may be achieved. This allows for the manufacture of only one or at most a very few sizes of prefilled containers to suit substantially all inflatable prosthesis requirements. However, the embodiments of FIGS. 1 through 4 and of FIGS. 5 and 6 are advantageous in that the same are simpler, non-electrical and substantially self-contained, and may provide accurate volumes of delivery if manufactured in a proper range of volumes for the particular purpose. In that regard, flexible containers such as shown in FIG. 1, if initially filled with a known air space above the fluid, can be used together with a volume scale on the side of the container to determine the amount of filling fluid left in the container when desired. In particular, if the container itself is transparent, a given volume of fluid in the container will in turn fill the same to a given level, so that the level of the fluid/air interface in the container at any particular time (when the same is not distorted by any pressurizing means) will provide an accurate measure of the volume of fluid left in the container (or for a reverse scale, the volume of fluid already delivered from the container). Similarly, as stated before, in an embodiment such as that of FIG. 5 and 6, if both the inner and outer enclosures are transparent, and the inner enclosure has a predetermined air space thereabove, the level of the fluid-air interface in the inner container will provide an accurate measurement of the fluid which has been delivered from the container and/or the amount of fluid remaining therein, as may be conveniently indicated by an appropriate scale printed on either the outer or inner container surface. This will be true for this embodiment even when the containers are pressurized.

Flexible containers such as for the delivery of IV solutions are well known in the prior art, and like the present invention, may be fabricated from any of various materials such as by way of specific example, PVC or polyethylene. Similarly, different types of pressure gauges and/or inflatable pumps may be used, such inflatable pumps being, by way of example, clear washable plastic or fabric reinforced materials, both of reusable and disposable types. Similarly, the same may be provided by the manufacturer in a sterile or a non-sterile condition. While the use of a peristaltic pump as shown in FIG. 8 is desirable because of its automatic accurate flow measuring characteristics, other embodiments might well utilize some other type of flow meter in the line so as to provide a measure of flow other than through the measure of fluid remaining in the flexible container or delivered by a positive displacement pump such as a peristaltic pump.

Finally, to provide an accurate measure of the pressure within the prosthesis during the inflation process without having to momentarily stop the pumping for pressures to equalize, one could utilize a dual port inflation tube in place of inflation tube 64, wherein one port delivers inflation fluid to the prosthesis from a higher pressure source while the second port senses the static pressure within the prosthesis for measurement by pressure transducer connected to that second port.

In the embodiments hereinbefore described, the actual pressurizing means for to pressurize the means for forcibly encouraging the inflation fluid from the container was a separate means such as a bulb, a peristaltic pump. etc. As an alternative, a container such as shown in FIG. 10 may be provided. Such a container may be filled with a propellant, such as a pressurized gas (nitrogen being a suitable example of such a gas) or a liquified gas under pressure to connect to embodiments such as shown in FIGS. 3 through 6 for encouraging the inflation fluid in the container outward through the flexible tube. Alternatively, the container of FIG. 10, either a flexible or a rigid container, may include both the propellant and prosthesis inflation fluid, with or without a separation bladder, so that the inflation fluid, the flexible tube and injection tube, and the energizing means may be provided by a manufacturer in a ready to use condition, minimizing surgery time and the opportunity for contamination and infection.

A further embodiment of the invention may be seen in FIG. 9. As shown in that figure, a syringe 72 having a fill tube 74 and a low range pressure gage 76 thereon (approximately 100 to 125 mm Hg full scale with a substantial overpressure survival capability) in communication with the pumping chamber of the syringe is provided for use in inflating mammary prostheses and tissue expanders, and which in turn may be refilled in any of a number of ways. During inflation of a tissue expander with the device shown, the surgeon may periodically stop applying force on the syringe plunger 78, whereupon the low range pressure gage 76 will quickly stabilize at a pressure reading corresponding to the pressure in the tissue expander. For filling the syringe, a syringe fill port 80 and a valve 82 are provided, the valve being moveable between a first position placing the interior pumping chamber of the syringe 72 in communication with the fill tube 74 for inflating mammary prostheses and tissue expanders, and a second position placing the interior pumping chamber of the syringe 72 in communication with the syringe fill port 80 for filling the syringe through the fill port. While the syringe fill port 80 does not have to be used to fill the syringe, the fill port 80 is convenient to use as it allows for the more rapid filling of the syringe because of its much larger internal diameter than the fill tube 74, whether the syringe is filled from a source of inflation fluid under pressure such as a pump or container under pressure, or merely from a non-pressurized supply of inflation fluid.

In the prior description, reference has been made to the fill tube on the end of the flexible tube for engaging a fill port on the inflatable mammary prosthesis or tissue expander (collectively referred to in the claims to follow as inflatable implantable prostheses). The fill tube may be in any of various forms, dependent on the form of fill port on the prosthesis with which the invention is to be used. Such fill ports include ports which must be pierced, and which then will be self sealing upon withdrawal of the piercing member. Thus for such applications, the fill tube typically will be in the form of a sharp tubular metal needle assembled onto the end of the flexible tube connectable to the filling fluid container. In other cases the fill port may be in the form of a self closing valve which can be opened by insertion of a blunt tube of appropriate size, in which case the fill tube may be in the form of a small, blunt metal or plastic tubular member on the end of the flexible tube. For this purpose, the fill tube may be a separate member assembled onto the flexible tube, or if the flexible tube is of limited flexibility such as a polyethylene tube, the fill tube may simply comprise the end section of the flexible tube, appropriately shaped and sized for insertion into the prosthesis valve. In any event, in the claims to follow, the fill tube, whether piercing or not and/or whether a separate member assembled onto the flexible tube or comprising the end portion thereof, is sometimes generally referred to as an injection tube and the port on the prosthesis an injection port.

Thus, while the present invention has been disclosed and described with respect to various preferred embodiments thereof, it will be understood by those skilled in the art that various changes in form and detail may be made therein without departing from the spirit and scope of the invention.

We claim:

1. A method of inflating an inflatable implantable prosthesis that has a fill port, comprising the steps of:
    (a) providing a flexible container that contains a volume of an inflation fluid, and is connected to an injection tube;
    (b) inserting said injection tube into the fill port of the inflatable implantable prosthesis;
    (c) pressurizing said inflation fluid to induce a continuous flow of said inflation fluid through said injection tube and into the inflatable prosthesis to entirely fill the inflatable prosthesis with a volume of inflation fluid provided entirely by the continuous flow of inflation fluid within said inflatable container without refilling said inflatable container;
    (d) closing the flexible tube in a non-destructive manner to terminate the flow of the inflation fluid; and,
    (e) pulling the injection tube out of the fill port such that the flexible container can be used to fill another implantable prosthesis.

2. The method of claim 1 wherein the volume of inflation fluid within said flexible container is approximately equal to the volume of inflation fluid that fills the inflatable prosthesis.

3. The method of claim 1 wherein said inflation fluid is pressurized by a peristaltic pump.

4. The method of claim 1 wherein said inflation fluid is pressurized by an inflatable member that applies a pressure to said inflatable container.

5. The method of claim 4 wherein the inflatable member is pressurized by a manually operated inflation bulb to pressurize said inflation fluid.

6. The method of claim 4 wherein the inflatable member is pressurized by a connection to a source of gas pressurized to a constant pressure to pressurize said inflation fluid.

7. The method of claim 1 further comprising the step of heating said inflation fluid before said inflation fluid flows through said injection tube and into the inflatable prosthesis.

8. The method of claim 1 wherein said flexible container includes a visible indicia for indicating a level of inflation fluid.

9. The method of claim 1 wherein said flexible container containing said inflation fluid and said flexible tube are provided in a sterile enclosure with said flexible container and said flexible tube being unconnected, the same to be connected at the time of use.

10. The method of claim 1 wherein said flexible container containing said inflation fluid and said flexible tube are provided preconnected and in a sterile enclosure.

11. The method of any one of claims 4, 5, 6, and 8 further comprising the step of hanging the flexible container containing the inflation fluid and the inflatable member on an IV stand.

12. A method of inflating an inflatable implantable prosthesis that has as fill port, comprising the steps of:
  (a) providing a flexible container that contains a volume of an inflation fluid, and is connected to an injection tube;
  (b) inserting the injection tube into said fill port of the inflatable implantable prosthesis;
  (c) elevating said flexible container above the inflatable prosthesis so that said inflation fluid continuously flows from said flexible container to the inflatable prosthesis, solely by a gravitational force, to entirely fill the inflatable prosthesis with a volume of inflation fluid provided entirely by the continuous flow of inflation fluid within said inflatable container without refilling said inflatable container;
  (d) closing the flexible tube in a non-destructive manner to terminate the flow of the inflation fluid; and,
  (e) pulling the injection tube out of the fill port such that the flexible container can be used to fill another implantable prosthesis.

13. The method of claim 12 wherein the volume of inflation fluid within said flexible container is approximately equal to a volume of inflation fluid that fills the inflatable prosthesis.

14. The method of claim 12, further comprising the step of heating said inflation fluid before said inflation fluid flows through said injection tube, and into the inflatable prosthesis.

15. The method of claim 12 wherein said flexible container includes a visible indicia for indicating a level of inflation fluid therein.

* * * * *